ic patent

United States Patent [19]
Lutz

[11] Patent Number: 4,959,867
[45] Date of Patent: Sep. 25, 1990

[54] AUDIOMETER ATTENUATION METHOD AND APPARATUS

[75] Inventor: William J. Lutz, Middleton, Wis.

[73] Assignee: Nicolet Instrument Corporation, Madison, Wis.

[21] Appl. No.: 231,115

[22] Filed: Aug. 11, 1988

[51] Int. Cl.$^5$ ............................................. H03G 3/00
[52] U.S. Cl. .................................. 381/107; 128/746; 381/60
[58] Field of Search ................. 381/104, 109, 107, 60; 128/746

[56] References Cited

U.S. PATENT DOCUMENTS

| | | |
|---|---|---|
| 4,107,465 | 8/1978 | Charlebois et al. |
| 4,239,938 | 12/1980 | Ponto ................................... 381/104 |
| 4,276,508 | 6/1981 | Usugi . |
| 4,448,074 | 5/1984 | Schmidt . |
| 4,515,169 | 5/1985 | Ward .................................... 128/746 |
| 4,726,067 | 2/1988 | Alonso ................................. 381/106 |
| 4,731,851 | 3/1988 | Christopher ......................... 381/104 |

FOREIGN PATENT DOCUMENTS 3008033 9/1981 Fed. Rep. of Germany ...... 128/746

OTHER PUBLICATIONS

Specification Sheet by Analog Devices for AD7545 CMOS 12-Bit Buffered Multiplying DAC, Digital-to-Analog Converters, vol. 1, 9–231 to 9–237.

Primary Examiner—Forester W. Isen
Attorney, Agent, or Firm—Foley & Lardner

[57] ABSTRACT

An audiometer is provided with attenuators which have two successive stages, a main attenuator providing a large range of attenuation and a second stage which is capable of providing silent switching and finely adjustable attenuation. The signal from the main attenuator in the first stage is provided through two signal paths in the second stage to two input terminals of the earphone, with the sound output from the earphone determined by the voltage across the two input terminals. The first of the signal paths includes a pad having fixed attenuation which provides a low level voltage output signal to the one input terminal, and the other signal path includes an adjustable attenuator which provides fine adjustment of the magnitude of the output signal across the earphones. The adjustable attenuator may include multiplying digital to analog converters which have an attenuation determined by their digital input word with the signal from the main attenuator provided as the voltage reference signal to the digital to analog converters. The attenuation may be controlled utilizing a microprocessor to provide the data words to the multiplying digital to analog converters. A switching circuit is provided on the output of the adjustable attenuator to disconnect the adjustable attenuator from the earphone when that attenuator's output is not required. This disconnection improves the signal to noise ratio for low level signal because the noise at the output of the adjustable attenuator does not contribute to the earphone signal. As a result, the available dynamic range is increased by the attenuation of the fixed attenuator. No clicks are produced when the adjustable attenuator is switched in or out.

18 Claims, 4 Drawing Sheets

AUDIOMETER ATTENUATION METHOD AND APPARATUS

FIELD OF THE INVENTION

The present invention pertains generally to hearing test instruments, and more particularly to attenuators for audiometers.

BACKGROUND OF THE INVENTION

An audiometer is used to test a subject's hearing over a range of frequencies and intensity levels. The audiometer creates an audio signal of a given frequency, intensity, and duration. The subject indicates to the test administrator if the audio signal was audible. The frequency range of the human ear is approximately 20 Hz to 20,000 Hz; however, it is typical that an audiometer can have a range of 125 Hz to 12,000 Hz. The human ear has a 120 db range, but the ear is not equally sensitive at all frequencies. This requires the electronics used to test hearing to have a somewhat larger dynamic range—135 db is typically required. This dynamic range exceeds that currently available from even the best amplifiers. The dynamic range of an amplifier is limited by its signal-to-noise ratio (SNR). The best SNR currently available is about 120 db. To get the dynamic range required, prior art audiometers insert a passive attenuator between the amplifier and the test earphone. The passive attenuator attenuates both the signal and the noise, thus allowing the audiometer to produce low-level signals at a reasonable SNR. Prior art audiometers switch these attenuators in or out using relays or solid-state switches. When the passive attenuator is switched into the circuit, the main attenuator is increased by the attenuation value of the passive attenuator. This increases the SNR at the earphone by the attenuation value of the passive attenuator. However, the main attenuator and the passive attenuator do not switch at the same rate (the main attenuator is faster). For a brief period of time, the output level will be too large. This produces the perception of a click, especially if the change is made while a signal is being presented. This problem is particularly severe at low power where the click produced by switching is comparable in power to the desired tone.

The undesired transient electronic clicking created by the switching of attenuators or pads in and out of the circuit is particularly troublesome in the von Bekesy test. In this test the subject depresses a button when the tone is audible, reducing the output power. When the power has been reduced to the point where the tone is inaudible the subject releases the button, increasing the power. When the tone is again audible, the subject again depresses the button, and the process repeats. Throughout the test the frequency is swept slowly from approximately 100 Hz to 10,000 Hz, and the maximum and minimum decibel levels at each frequency are recorded. The hearing threshold for a particular frequency is taken as the average of the maximum and minimum decibel levels.

A subject typically has a hearing threshold that increases with frequency. Thus, as frequency increases the subject eventually cannot hear the output, and must depress the button to increase the output power. To increase the power, attenuators must be switched, often creating an audible click having approximately the same power as the output tone. The test subject could interpret the audible click as part of the test, and release the button even though the tone is not audible. This results in inaccurate measuring of the hearing threshold, and could possibly result in the subject causing the power output to oscillate about the decibel level where attenuators are changed. Even if the subject recognizes that the click is not part of the test, it is still distracting and could cause error to be introduced into the test.

SUMMARY OF THE INVENTION

In accordance with the principles of the present invention, an audiometer is provided with an "active attenuator" between the amplifier and the earphone, instead of the prior-art passive attenuator. This attenuator preferably covers a 40 db range with 0.1 db step size. As the attenuation of the circuit is varied between 0 db and 40 db, the noise performance of the circuit is that of the adjustable attenuator. At the boundary of 40 db, the adjustable attenuator is switched out (in a clickless fashion) to produce a circuit that is equivalent to a passive attenuator. The changeover from active circuit to passive attenuator is done in such a way that no clicks or other artifacts are produced, even if a tone is being presented while the change is being made. It should be noted that first the "active attenuator" is used over a 40 db range, and then the main attenuator is used to decrease the signal level even further. Thus, use of the "active attenuator" does not require a corresponding adjustment of the main attenuator while it is being used over its 40 db range.

Like the passive attenuator, this invention increases the available dynamic range by 40 db. However, the circuit has a significant advantage over the passive attenuator approach. Because the circuit has very fine steps and because the circuit does not require a corresponding adjustment of the main attenuator, the circuit produces no clicks or artifacts as the level of the signal is changed.

The first stage or main attenuator has a total voltage output signal range of about 100 db with typical 1 db switching steps. The second stage has a range of 40 db in steps preferably about 0.1 db or less. The second stage consists of a switchable gain unit to increase the range, a pad to provide a signal to one terminal of the earphone, and an adjustable attenuator to provide a signal to a second terminal on the earphone. The adjustable attenuator is capable of making 0.1 db steps quickly and silently. The earphone is preferably of the type which functions as a "floating load"; that is, neither terminal of the earphone needs to be at circuit ground. The earphone responds to the difference in voltage across its terminals to effectively sum the two signals at the two terminals. The signal from the adjustable attenuator is provided to the earphone terminal through a switching circuit which can be controlled to connect or disconnect the adjustable attenuator from the earphone terminal without creating audible clicks in the earphone. When going down in level through the 40 db boundary at which the adjustable attenuator is to be disconnected, the switching circuit momentarily grounds both the second earphone terminal and the output of the adjustable attenuator and then disconnects the adjustable attenuator from the earphone terminal. When going up in level through the 40 db boundary, the adjustable attenuator is reconnected to the second earphone terminal while the terminal is still grounded, and shortly thereafter, the second terminal is disconnected from the ground. This switching procedure ensures that no clicks are generated as the adjustable attenuator is inserted in or removed from the circuit. The adjustable attenuator is removed from the circuit below the 40 db boundary so that the noise from the amplifier in the adjustable attenuator does not degrade the signal to noise ratio of low level output signals.

Further object, features and advantages will be apparent from the following description when taken in conjunction with the accompanying drawings.

DESCRIPTION OF THE PREFERRED EMBODIMENT

Figure 1:
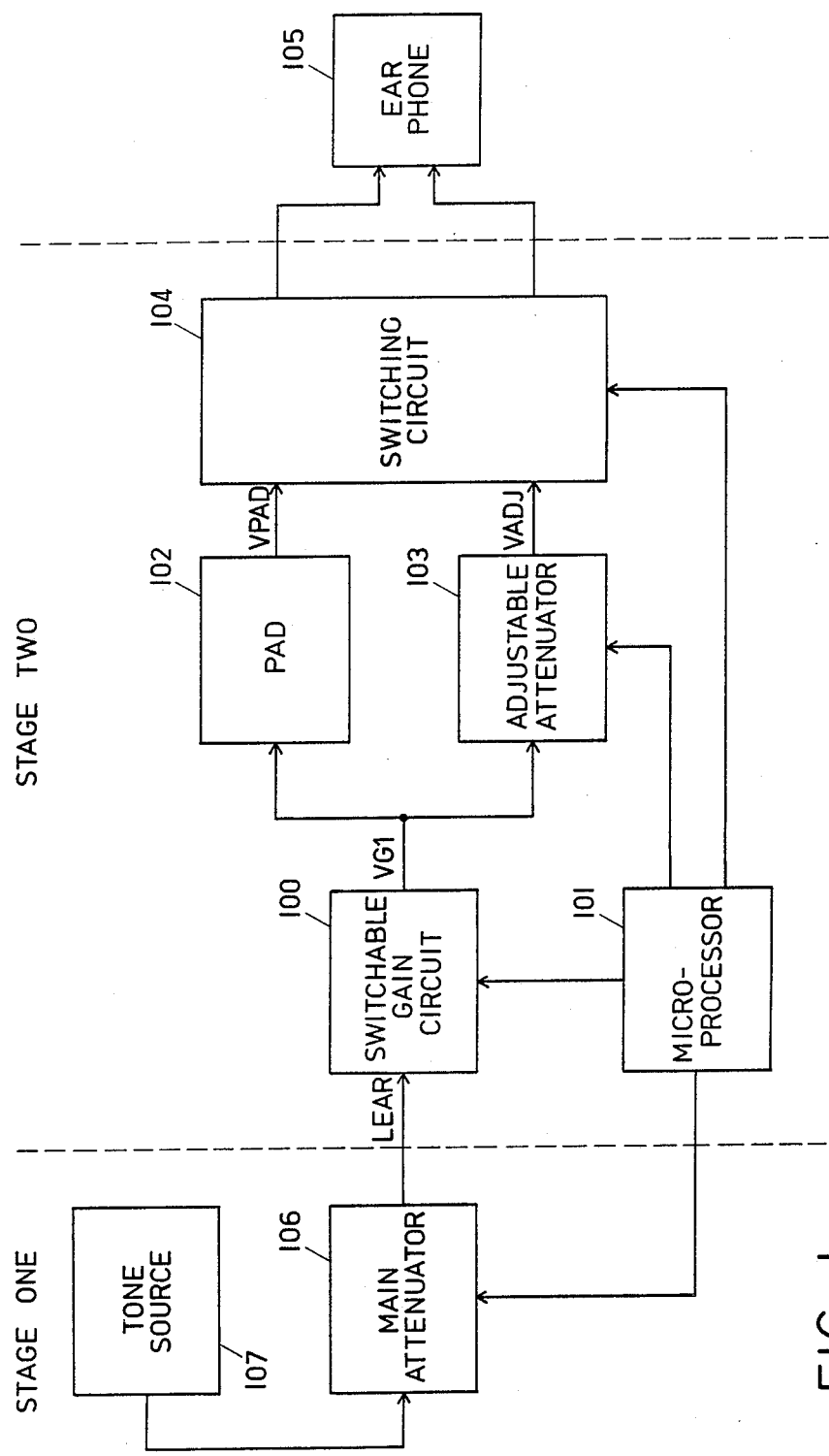
FIG. 1 is a block diagram of the silent switching audiometer attenuation apparatus of the invention.

With reference to the drawings, an attenuator apparatus for an audiometer in accordance with the present invention is shown in block diagram form in FIG. 1. The attenuator apparatus includes a switchable gain unit 100, described further below, which includes a switch (not shown in FIG. 1) which may be operated either manually or under the control of a microprocessor 101 to allow the gain to be changed. The switchable gain unit 100 is used to compensate for the different sensitivities of the earphones and the insert earphones. The input voltage to the gain unit 100 typically has a range of frequencies from approximately 100 Hz to 10,000 Hz and a voltage magnitude range of 100 dB, in steps generally of 1 db. The output of the gain unit 100 is supplied to a fixed attenuator or pad 102 and an adjustable attenuator 103. The input signal to the switchable gain unit 100 is received from a main attenuator 106 which receives a tone signal at a reference level from a tone source 107. The tone source or generator 107 and the main attenuator 106 are of well known standard design as used in conventional audiometers.

The pad 102 is connected to provide its output voltage to one terminal of an earphone 105 (or insert earphone if one is used) and provides a voltage to the earphone that is a fixed percentage of the output voltage of the gain unit 100 (e.g., −40 db).

The adjustable attenuator 103 is capable of providing an output voltage that ranges in magnitude from zero volts to as high as the output voltage of the gain unit 100. The attenuation steps may be as small as 0.1 dB. A switching circuit 104 prevents transient electronic clicks from being heard in the earphones 105 when the adjustable attenuator 103 is switched in or out of the circuit.

The earphones 105 are of the type commonly used with audiometers and may be replaced with insert earphones. The earphones 105 (or insert earphones) have two input terminals and produce a sound pressure level proportional to the difference in voltage applied to these two terminals.

Figure 2:
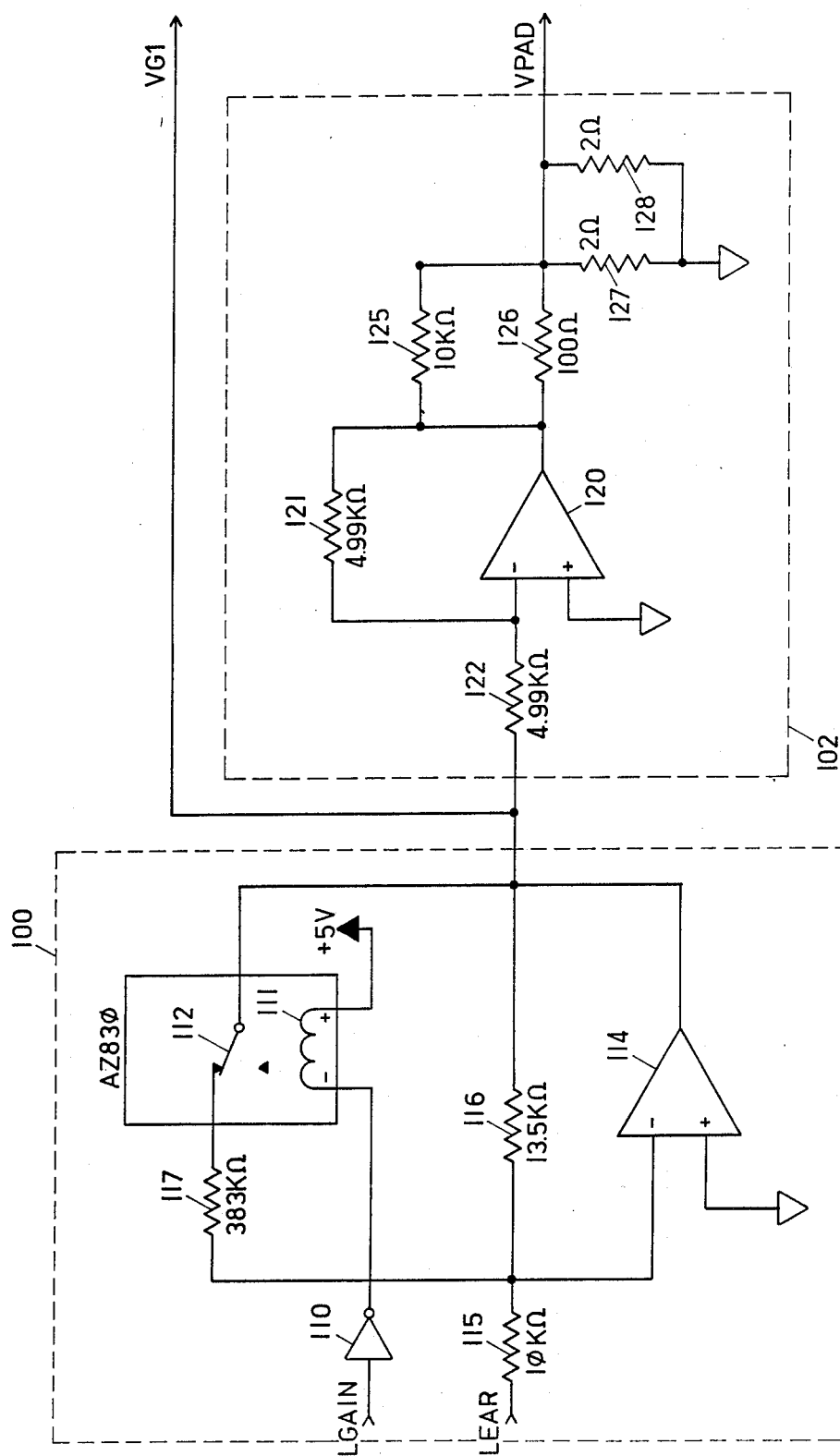
FIG. 2 is a circuit diagram of a portion of the second stage circuit.

FIG. 2 shows a circuit diagram of the switchable gain unit 100 and the pad 102. There are two input signals provided to the gain unit 100. LGAIN is a control signal from the microprocessor 101 that is passed through an invertor 110 to a relay coil 111 to turn the switch 112 open or closed. LEAR is an input voltage having a range of frequencies and magnitudes. The gain unit 100 includes an operational amplifier 114, an input resistor 115 receiving the signal LEAR, a primary feedback resistor 116, and a secondary feedback resistor 117 which is connected in parallel with the resistor 116 when the relay switch 112 is closed. When the signal LGAIN is LOW (0 volts), the inverter 110 provides a HIGH (5 volts) output. This maintains the switch 112 in the closed (up) position, placing the resistor 117 in parallel with the resistor 116. The parallel combination of resistors 116 and 117 has an effective resistance preferably equal to that of the input resistor 115 (e.g., 10K ohms). Thus, the output signal VG1 from the gain unit 100, when LGAIN is low, is equal to −LEAR.

When LGAIN is HIGH, the inverter 110 has an output that is LOW, placing the switch 112 in its open position removing the resistor 117 from the feedback circuit. The operational amplifier 114 continues to act as an inverter, but has a higher than unity gain (e.g., 1.35). Thus, the output VG1 of the gain unit 100, when LGAIN is HIGH, is equal to $-A \times \text{LEAR}$, where an amplification factor A is equal to the quotient of the resistances of resistors 116 and 115.

The pad 102 includes an inverting amplifier 120 with its non-inverting input connected to ground, a resistor 121 connected as a feedback resistor between the output and the inverting input, and a resistor 122 connected between the output of the gain unit 100 and the inverting input of the amplifier 120. The amplifier 120 provides an output signal sufficient to drive the earphones.

In the preferred embodiment, the resistors 121 and 122 are both equal (e.g., 4.99 kohms). Various resistance values may be used to obtain appropriate input and output impedances, preferably with the same value used for both resistors to obtain unity gain from the amplifier. The output of the amplifier 120 is provided to a voltage divider which includes the parallel combination of resistors 125 and 126 (for example, having resistance values of 100 ohms and 10 kohms) and the parallel combination of a resistor 127 and a resistor 128 connected to ground (for example, each of 2 ohm resistance). With the foregoing exemplary resistance values, the voltage divider has an output voltage (VPAD) equal to 1% of its input voltage, LEAR (−40 db attenuation). The output voltage VPAD is supplied directly to the first input terminal of the earphone 105.

Figure 3:
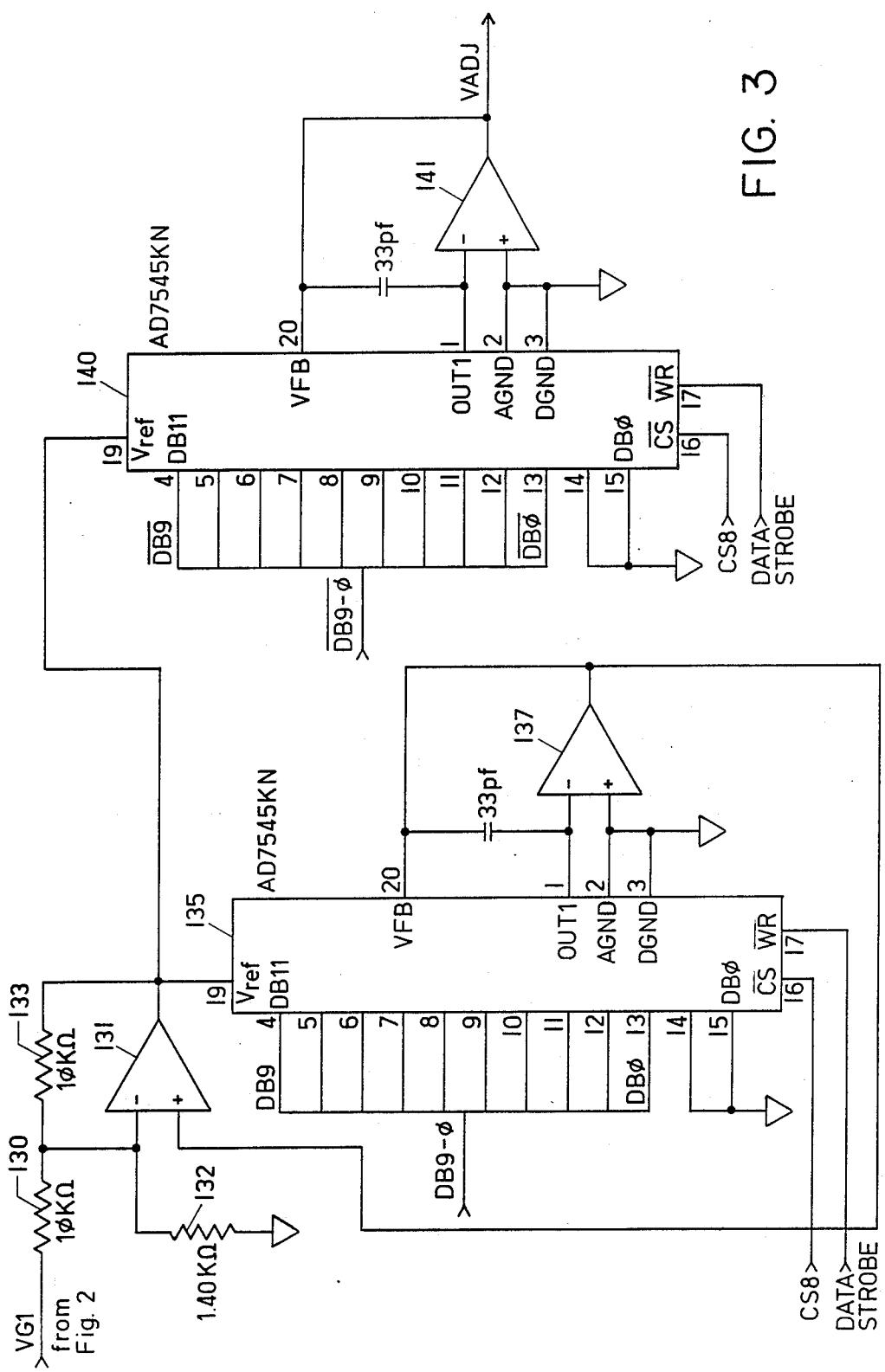
FIG. 3 is a circuit diagram of the second stage adjustable attenuator.

The output VG1 of the switchable gain unit 100 also is supplied to an adjustable attenuator 103, shown in a circuit diagram in FIG. 3. The signal VG1 is passed through an input resistor 130 to the inverting input of an operational amplifier 131, which is also connected to ground through a resistor 132, with a feedback resistor 133 connected between the output and the input of the amplifier. A multiplying digital-to-analog converter (MDAC) 135, (e.g. an AD 7545KN, described in Vol. 1, pages 9-231 to 9-237 of *Digital-to-Analog* converters by Analog Devices) is connected to provide feedback from the output of the operational amplifier 131 to the non-inverting terminal of the amplifier. The analog reference voltage to MDAC input is the output voltage of the amplifier 131. The digital input (DB9-0) is supplied by the microprocessor to digits DB2-DB11 of the MDAC binary word input. Digits 1 and 0 of the MDAC binary word input are connected directly to ground to give them a constant value of zero. An operational amplifier 137 is connected to the analog output of the MDAC 135 and supplies its output to the noninverting input of the amplifier 131. When the MDAC 135 is used in this manner, the output of the amplifier 137 is equal to $-V_{in} \times B$, (as described at Vol. 1, 9–234, *Digital to Analog Converters*) where B is the decimal equivalent of the MDAC binary word input divided by 4096 (i.e., the full digital input range). Thus, if the digital word from the microprocessor was 1000 0000 00, the MDAC binary word would be 1000 0000 0000, B would equal 2048/4096=0.5, and Vout would equal $-0.5 \times V_{in}$. Therefore, the voltage at the non-inverting terminal of the amplifier 131 would equal the output voltage of the amplifier multiplied by $-B$. If resistors 130 and 131 each are 10k ohms, and resistor 132 is 1.4k ohms, the output voltage of the amplifier 137 is equal to $-VG1/(1+9.1B)$, which is equal to $LEAR/(1+9.1B)$.

The output voltage of the operational amplifier 131 is supplied as the analog input voltage to an MDAC 140 (which may also be an AD7545KN). The MDAC 140 is connected to provide an output voltage equal to the analog input voltage multiplied by the MDAC input binary word divided by the full digital input range, e.g., 4096 (B2). The digital input to the MDAC 140 is the digital input to the MDAC 135 inverted; for example, if the digital input to MDAC 135 were 1000 0000 00, the digital input to MDAC 140 would be 0111 1111 11. Since the two least significant digits in the MDAC 140 binary word are grounded, the complete MDAC 140 binary word would be 0111 1111 1100. It is readily seen that the sum of the MDAC 135 binary word (BW135) and the MDAC 140 binary word (BW140) will equal 1111 1111 1100 (or decimal 4092, since the digital input to the MDAC 140 is the digital input to the MDAC 135 inverted). Thus

| | | |
|---|---|---|
| since | B = | BW135/4096 |
| and | B2 = | BW140/4096 |
| then | B + B2 = | (BW135 + BW140)/4096 |
| | B + B2 = | 4092/4096 |
| | B + B2 = | 1 (within 0.1%) |
| | B2 = | 1-B. |

Thus, the output voltage of VADJ of the operational amplifier 141, which is connected to the analog output of the MDAC 140, is equal to the output voltage of the operational amplifier 131 multiplied by $-(1-B)$, or $$VADJ = -(1-B)/(1+9.1B) \, LEAR$$

Since B is determined by the 10 bit digital word supplied by the microprocessor, it is possible to create very small changes in B. The total range of B is $0 \leq B \leq 1$ and the smallest possible change that may occur in B is 4/4096 or about 0.1%. This circuit is characterized by an attenuation whose db value is approximately proportional to B. A look-up table stored in PROM memory associated with the microprocessor 101 may be used by the microprocessor to provide digital inputs to the MDACs 135 and 140 which will yield a desired level of attenuation and a linear attenuator.

Since 0.01 LEAR is supplied to the first difference terminal, the total voltage difference Vphone supplied to earphone 105 is $$Vphone = Vpad - VADJ$$

$$Vphone = [(1-B)/(1+9.1B) + 0.01] LEAR$$

and the total gain is $$GAIN = (1-B)/(1+9.1B) + 0.01$$

Because small changes in B are possible, 0.1 db steps in the gain of the second stage are possible. The digital word is selected by the microprocessor in a manner to ensure 0.1 db steps over the entire gain range (from 0.01 to 1.01). The table below shows values of B, the digital word supplied by the microprocessor, and the changes in B and the digital word to maintain 0.1 db steps for various gains.

| GAIN | B | DIGITAL WORD | CHANGE IN B | DIGITAL CHANGE |
|---|---|---|---|---|
| 1.01 | 0.00 | 0000 0000 00 | 0.0012 | 0000 0000 01 |
| 0.10 | 0.50 | 1000 0000 00 | 0.017 | 0000 0100 01 |
| 0.01 | 1.00 | 1111 1111 11 | 0.022 | 0000 0101 11 |

It can be seen that over the entire range of gain it is possible to have 0.1 db steps in the gain by using the appropriate microprocessor provided digital word. The small changes in VADJ insure that electronic clicks are not created when the VADJ is changed by changing the attenuation provided by the adjustable attentuator 103.

Figure 4:
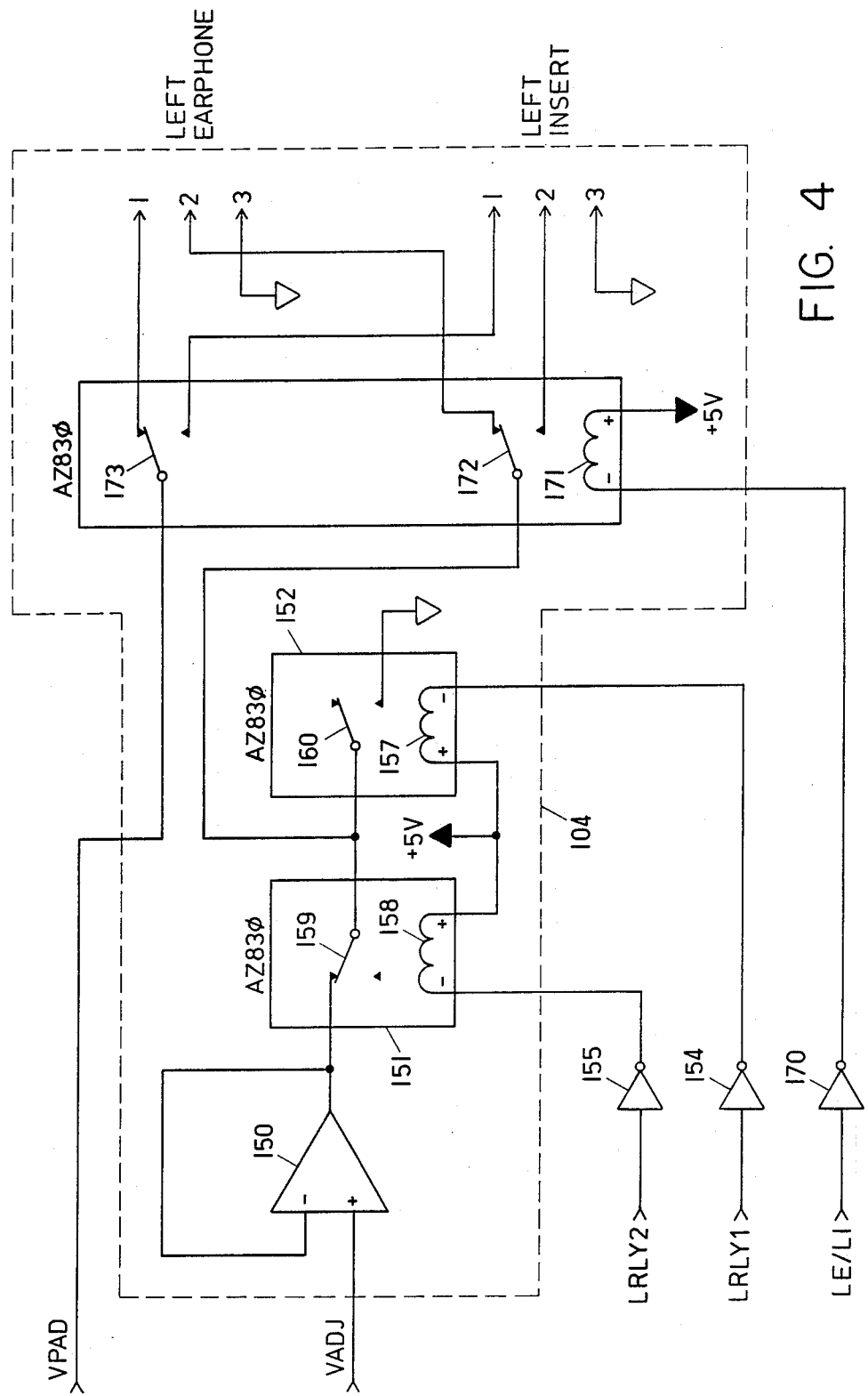
FIG. 4 is a circuit diagram of the switching circuit that provides switching of the connection of the adjustable attenuator and the earphone without creating an audible sound in the earphone.

As shown in FIG. 4, VADJ is supplied to the non-inverting input of an operational amplifier 150 which is connected to act as a unity gain voltage follower. The output of the amplifier is connected to relay switches 151 and 152, which act to prevent transient electronic clicks, from being created when the adjustable attenuator is switched which could otherwise result in an audible click in the earphones.

During such operation (when VADJ is changing and LEAR is constant), control signals LRLY2 and LRLY1, provided by a microprocessor, are both LOW. Inverters 154 and 155 receive the signals LRLY1 and LRLY2, respectively and provide the inverted signals to control coils 157 and 158 in the relays 152 and 151, respectively. When the inputs LRLY1 and LRLY2 are HIGH, the outputs of the inverters 154 and 155 are LOW, and the relay switches 159 and 160 are both OFF (up) so that the output of the amplifier 150, the signal VADJ, is connected to the second difference terminal of the ear phones 105.

The disconnection of the adjustable attenuator from the earphone terminal is done in such a way that no clicks or other artifacts are produced. When the adjustable attenuator 103 is being used over its 40 db range, the amplifier 150 is connected to the earphone terminal. At the 40 dB boundary, the amplifier 150 is no longer providing a signal to the earphone 105. To improve the signal to noise ratio, this amplifier is switched out of the circuit in a way that does not create clicks or artifacts. This changeover is accomplished in the following manner. First, the control signal LRLY1 is changed by the microprocessor 101 to HIGH, causing the output of the inverter 154 to be LOW. This turns ON switch 160, temporarily connecting the output of the amplifier 150 to ground, as well as grounding the second difference terminal of the earphone 105. This causes no damage because at this time the output of the amplifier 150 is at zero volts (ground). Several milliseconds later the control signal LRLY2 is changed to HIGH, causing the output of the inverter 155 to be LOW, and turning the switch 159 ON. At this point in time the output of the amplifier 150 is disconnected from the grounded second difference terminal and from the earphone 105. Again, there is no voltage transient produced to cause a click in the earphone because the relay 160 maintains the earphone terminal connected to ground. Thus, the amplifier 150 has been disconnected from the earphone 105 in a clickless fashion. The noise from the amplifier 150 is thus not passed to the earphone and the signal to noise ratio is improved by 40 dB.

To re-engage the active attenuator, the output of the amplifier 150 must be reconnected to the lower terminal of the earphone 105. This must be done in the reverse order of the sequence described above. While this changeover is being done, the output of the amplifier 150 (Vadj) is set to zero volts. When it is desired to reconnect the amplifier 150, first the control signal LRLY2 is made LOW. This causes the output of the inverter 155 to be HIGH, which then causes the relay switch 159 to connect the output of the amplifier 150 to the lower terminal of the earphone 105. The lower terminal of the earphone is held at ground by the relay switch 160 when this is done, so no click or artifact occurs. Several milliseconds later (to allow the contacts of relay 159 to stop bouncing), the control signal LRLY1 is changed to LOW, causing the output of inverter 154 to be high, and turning the relay switch 160 off. This removes the ground from the lower terminal of the earphone 105. The signal Vadj can now be increased as desired, causing a larger sound pressure level to be produced by the earphone 105.

Another control signal, LE/LI, is provided from the microprocessor, or from a manual control switch (not shown) through an inverter 170 to a relay coil 171. When the output of the inverter 170 is low, the coil 171 is inactivated, and the switches 172 and 173 are in their positions shown in FIG. 4, connecting the output signal to the (left) earphone. When the control signal LE/LI goes low, the coil 171 is activated and the switches 172 and 173 are switched to provide the output signal to the (left) insert, when desired by the operator.

The present invention is particularly useful for a von Bekesy test. The Bekesy test requires that the intensity level of the test signal be changed while the signal is being presented to the subject. Transient click problems are avoided, while at the same time the accuracy of the test is increased since smaller steps are used for increasing or decreasing the output.

The prior art problem of transient clicks is avoided since the 0.1 db steps generated by the adjustable attenuator do not create transient electronic clicks. When the required intensity level of the test signal is sufficiently low, the active adjustable attenuator is disconnected from the earphone. This results in an improvement of the signal to noise ratio, e.g., of 40 dB for the circuit described above. The changeover is accomplished by the activation of the relays 151 and 152 in the manner described above. The time required to produce a changeover in this manner may be approximately 10 milliseconds or less.

It is understood that the invention is not confined to the embodiment set forth herein as illustrative, but embraces such modified forms thereof as come within the scope of the following claims.

What is claimed is:

1. Attenuation apparatus for an audiometer of the type having an earphone with at least two input terminals with the sound output determined by the difference voltage between the input terminals, a tone signal source which provides a selected tone, and a main attenuator which attenuates the volume of the tone in steps to provide an output signal for transmission to the earphone, comprising;
    (a) means for receiving the tone signal from the main attenuator and providing a selected low range signal to a first one of the input terminals of the earphone;
    (b) adjustable attenuator means for receiving the signal from the main attenuator and providing an output signal to the other second input terminal of the earphone at a controllable level of attenuation, the means including a multiplying digital-to-analog converter having a digital word input, a digital input magnitude range, and an analog voltage reference input connected to receive the tone signal from the main attenuator, the analog voltage output of the multiplying digital to analog converter connected to provide its signal to the second terminal of the earphone, the output of the multiplying digital-to-analog converter being equal to the analog input signal times a fraction equal to the digital input word magnitude divided by the digital input magnitude range of the multiplying digital-to-analog converter.

2. The attenuation apparatus of claim 1 wherein the means for providing the tone signal to the first terminal of the earphone includes a pad having fixed attenuation.

3. The attenuation apparatus of claim 1 further including switchable gain means, connected to receive the tone signal from the main attenuator, for providing an output signal to the means for receiving the tone signal and providing a selected low range signal and also to the adjustable attenuator means, the switchable gain means controllable to provide one of at least two levels of gain to the signal passed therethrough.

4. The attenuation apparatus of claim 1 including switching means, connected to receive the output of the adjustable attenuator means for providing an output signal to the second terminal of the earphone, the switching means including two control signal responsive switches with one switch connected between the adjustable attenuator means and the second terminal of the earphone and the other connected between the second terminal of the earphone and ground, and including means for controlling the switches such that the one switch connected to ground may be switched to connect the output of the adjustable attenuator means and the second terminal of the earphone momentarily to ground and for controlling the second switch to switch thereafter to disconnect the adjustable attenuator means from the second terminal of the earphone and from the grounded first switch, whereafter the attenuation of the attenuator means may be reset without passing electronic transient signals through to the earphone.

5. The attenuation apparatus of claim 1 further including a microprocessor connected to control the attenuation of the adjustable attenuator means.

6. The attenuation apparatus of claim 1 wherein the adjustable attenuator means includes two multiplying digital to analog converters and a differential operational amplifier, a first of the multiplying digital to analog converters being connected in a feedback loop from the output to the noninverting input of the differential operational amplifier, and means for biasing the amplifier to provide a gain from the amplifier that is a function of the digital input word provided to the first multiplying digital to analog converter, the second multiplying digital to analog converter having a digital input magnitude range and connected to the output of the differential operational amplifier to receive the signal from the amplifier as its voltage reference input and arranged to provide a voltage output signal which is the product of its voltage reference input signal and a fraction equal to its digital input word divided by the digital input magnitude range.

7. Attenuation apparatus for an audiometer of the type having an earphone with at least two input terminals with the sound output from the earphone determined by the difference voltage between the input terminals, a tone signal source which provides a selected tone, and a main attenuator which attenuates the volume of the selected tone in steps to provide an output signal for transmission to the earphone, comprising:
(a) means for providing the tone signal from the main attenuator at a selected fixed low level to a first of the input terminals of the earphone;
(b) adjustable attenuator means for receiving the tone signal from the main attenuator and providing its output at a controlled variable attenuation;
(c) switching means, connected to the output of the adjustable attenuator means and connected to provide its output signal to the second terminal of the earphone, including a first switch connected between ground and the second terminal of the earphone and a second switch connected between the output of the adjustable attenuator means and the second terminal of the earphone, and means for controlling the two switches to cause the switch connected to ground to connect the second terminal of the earphone and the output of the adjustable attenuator means to ground at the time that the adjustable attenuator is set to provide zero output voltage, and for controlling the second switch to thereafter disconnect the adjustable attenuator means from the second terminal of the earphone and from the first switch so that the adjustable attenuator means is disconnected from the earphone, and thereafter when the adjustable attenuator is to be reconnected, to reconnect the output of the adjustable attenuator means to the second terminal of the earphone and to the first switch and thereafter to open the first switch to release the voltage level at the second terminal to the earphone from ground to the voltage level from the output of the adjustable attenuator means.

8. The apparatus of claim 7 wherein the means for providing the tone signal to the first earphone input terminal includes a pad having fixed attenuation.

9. The attenuation apparatus of claim 7 further including switchable gain means, connected to receive the tone signal from the main attenuators for providing an output signal to the means for providing the tone signal to the first terminal and to the adjustable attenuator means, the switchable gain means controllable to provide one of at least two levels of gain to the signal passed therethrough.

10. The attenuation apparatus of claim 7 further including a microprocessor connected to control the attenuation of the adjustable attenuator means.

11. The attenuation apparatus of claim 7 wherein the adjustable attenuator means includes two multiplying digital to analog converters and a differential operational amplifier, a first of the multiplying digital to analog converters being connected in a feedback loop from the output to the noninverting input of the differential operational amplifier, and means for biasing the amplifier to provide a gain from the amplifier that is a function of the digital input word provided to the first multiplying digital to analog converter, the second multiplying digital to analog converter having a digital input magnitude range and connected to the output of the differential operational amplifier to receive the signal from the amplifier as its voltage reference input and arranged to provide a voltage output signal which is the product of its voltage reference input signal and a fraction equal to its digital input word magnitude divided by the digital input magnitude range.

12. A method for switching signals in an audiometer of the type having an earphone with at least two input terminals, with the sound output from the earphone determined by the difference voltage between the input terminals, a tone signal source which provides a selected tone, and a main attenuator which attenuates the volume of the tone in steps to provide an output signal for transmission to the earphone, and two signal paths from the main attenuator to the two terminals of the earphone with one of the signal paths having an adjustable attenuator means therein for changing the attenuation of the signal applied therethrough to the second terminal in small steps, comprising the steps of:
(a) while the output of the adjustable attenuator means is providing substantially zero volts, connecting the output of the adjustable attenuator means and the second earphone input terminal to ground,
(b) within a selected short period of time thereafter, disconnecting the adjustable attenuator means from the second terminal and maintaining the second terminal connected to ground.

13. The method of claim 12 including the additional steps of:
(1) while the output of the adjustable attenuator means is at substantially zero volts, connecting the output of the adjustable attenuator means to the second terminal of the earphone while the second terminal is still connected to ground; and
(2) within a selected short period of time thereafter, disconnecting the second terminal from ground so that the voltage at the second terminal is at the voltage output of the adjustable attenuator means.

14. Attenuation apparatus for an audiometer of the type having an earphone with at least two input terminals with the sound output determined by the difference voltage between the input terminals, a tone signal source which provides a selected tone, and a main attenuator which attenuates the volume of the tone in steps to provide an output signal for transmission to the earphone, comprising:
(a) means for receiving the tone signal from the main attenuator and providing a selected fixed attenuation to the tone signal to provide a low range signal to a first of the input terminals of the earphone;
(b) adjustable attenuator means for receiving the signal from the main attenuator and providing an output signal to the second input terminal of the earphone at a controllable level of attenuation, which can be controlled to provide substantially zero voltage output from the adjustable attenuator means; and
(c) switching means for selectively connecting the adjustable attenuator means to and disconnecting it from the earphone terminal during times when the output of the adjustable attenuator means is substantially at zero volts.

15. The attenuation apparatus of claim 14 wherein the means for providing the tone signal to the first terminal of the earphone includes a pad having fixed attenuation.

16. The attenuation apparatus of claim 14 wherein the switching means is connected to receive the output of the adjustable attenuator means and for providing an output signal to the second terminal of the earphone, the switching means including two control signal responsive switches with one switch connected between the adjustable attenuator means and the second terminal of the earphone and the other connected between the second terminal of the earphone and ground, and including means for controlling the switches such that the one switch connected to ground may be switched to connect the output of the adjustable attenuator means and the second terminal of the earphone momentarily to ground and for controlling the second switch to switch thereafter to disconnect the adjustable attenuator means from the second terminal of the earphones and from the grounded first switch, whereafter the attenuation of the attenuator means may be reset without passing electronic transient signals through to the earphone.

17. The attenuation apparatus of claim 14 further including a microprocessor connected to control the attenuation of the adjustable attenuator means.

18. The attenuation apparatus of claim 14 wherein the adjustable attenuator means includes two multiplying digital to analog converters and a differential operational amplifier, a first of the multiplying digital to analog converters being connected in a feedback loop from the output to the noninverting input of the differential operational amplifier, and means for biasing the amplifier to provide a gain from the amplifier that is a function of the digital input word provided to the first multiplying digital to analog converter, the second multiplying digital to analog converter having a digital input magnitude range and connected to the output of the differential operational amplifier to receive the signal from the amplifier as its voltage reference input and arranged to provide a voltage output signal which is the product of its voltage reference input signal and a fraction equal to its digital input word divided by the digital input magnitude range.

* * * * *

UNITED STATES PATENT AND TRADEMARK OFFICE
CERTIFICATE OF CORRECTION

PATENT NO. : 4,959,867
DATED : September 25, 1990
INVENTOR(S) : William J. Lutz It is certified that error appears in the above-identified patent and that said Letters Patent is hereby corrected as shown below:

Column 8, line 10, delete "other".

Column 9, line 48, add --attenuation-- after "The" and before "apparatus".

Signed and Sealed this

Thirteenth Day of July, 1993

Attest:

MICHAEL K. KIRK

*Attesting Officer*     *Acting Commissioner of Patents and Trademarks*